(12) United States Patent
Hassad

(10) Patent No.: US 10,916,338 B2
(45) Date of Patent: Feb. 9, 2021

(54) METHOD FOR MANAGING A PHARMACEUTICAL SUPPLY CHAIN

(71) Applicant: Omar Hassad, Tinley Park, IL (US)

(72) Inventor: Omar Hassad, Tinley Park, IL (US)

( * ) Notice: Subject to any disclaimer, the term of this patent is extended or adjusted under 35 U.S.C. 154(b) by 177 days.

(21) Appl. No.: 16/128,291

(22) Filed: Sep. 11, 2018

(65) Prior Publication Data

US 2019/0147994 A1 May 16, 2019

Related U.S. Application Data

(60) Provisional application No. 62/584,506, filed on Nov. 10, 2017.

(51) Int. Cl.
*G16H 20/10* (2018.01)
*G16H 10/60* (2018.01)
*G16H 40/20* (2018.01)
*G06Q 30/06* (2012.01)

(52) U.S. Cl.
CPC .......... *G16H 20/10* (2018.01); *G06Q 30/0611* (2013.01); *G16H 10/60* (2018.01); *G16H 40/20* (2018.01)

(58) Field of Classification Search
CPC ........ G16H 10/60; G16H 20/10; G16H 50/20; G16H 40/20; G06Q 10/20; G06Q 20/10; G06Q 30/0222; G06Q 30/0283; G06Q 30/04; G06Q 30/0601
USPC .......................................................... 705/3
See application file for complete search history.

(56) References Cited

U.S. PATENT DOCUMENTS

| 6,014,631 A * | 1/2000 | Teagarden | G06Q 30/02 705/3 |
| 2006/0149416 A1* | 7/2006 | Mohapatra | G16H 40/63 700/242 |
| 2011/0251850 A1* | 10/2011 | Stephens | G06F 19/3462 705/2 |
| 2013/0144649 A1* | 6/2013 | Kalies, Jr. | G06Q 50/24 705/2 |

\* cited by examiner

*Primary Examiner* — Hiep V Nguyen

(57) ABSTRACT

A method for managing a pharmaceutical supply chain creates channels of communication between a plurality of user accounts including, a plurality of consumer accounts, a plurality of pharmacy accounts, and a plurality of wholesaler accounts managed by at least one central server for the transference of pharmaceutical medications. Through an online portal, a pharmaceutical medication inquiry is received by the at least one central server through a personal computing device associated with a specific consumer account. The pharmaceutical medication inquiry is assessed by users of the plurality of pharmacy accounts to offer a pharmaceutical medication bid to the user of the specific consumer account. If the user of the specific consumer account affirms the pharmaceutical medication bid, a contact exchange function is executed to exchange contact data of the specific consumer account and the pharmacy account corresponding to the lowest pharmaceutical medication bid for the users to arrange the transaction.

10 Claims, 13 Drawing Sheets

METHOD FOR MANAGING A PHARMACEUTICAL SUPPLY CHAIN

The current application claims a priority to the U.S. Provisional Patent application Ser. No. 62/584,506 filed on Nov. 10, 2017.

FIELD OF THE INVENTION

The present invention relates generally to a method for managing distribution of pharmaceutical medications. More specifically, the present invention relates to an online market place for a supply chain where consumers acquire pharmaceutical medications from local pharmacies and pharmacies to acquire pharmaceutical medications from wholesalers.

BACKGROUND OF THE INVENTION

Many people rely on pharmaceutical medications on a daily basis or as prescribed by a medical professional to manage a plurality of ailments. These pharmaceutical medications are often acquired at a local pharmacy for convenience to the consumer imbibing the pharmaceutical medication; however, the local pharmacy may not always have the desired pharmaceutical medication in stock when the consumer attempts to acquire the desired pharmaceutical medication. In such instances, the consumer would need to wait for the desired pharmaceutical medication to be restocked in the local pharmacy or would need to travel to another pharmacy to acquire the desired pharmaceutical medication. To restock, the local pharmacy places an order with a wholesaler. The wholesaler receives the order and provides an invoice for any goods shipped to the pharmacy.

The present invention is a method for managing a pharmaceutical supply chain through an online marketplace for consumers to locate and procure pharmaceutical medications from local pharmacies, for pharmacies to locate and restock pharmaceutical medications from wholesalers, and for wholesalers to distribute pharmaceutical medications to pharmacies. The present invention implements a blind bidding process to reduce prices as effectively as possible along the chain of distribution between wholesalers and pharmacies, between pharmacies and other pharmacies, and between consumers and pharmacies. Once the blind bid is accepted by the parties, the contact information between parties is distributed and the transaction of goods may occur.

DETAIL DESCRIPTIONS OF THE INVENTION

All illustrations of the drawings are for the purpose of describing selected versions of the present invention and are not intended to limit the scope of the present invention.

The present invention is a method for managing a pharmaceutical supply chain. The present invention utilizes an online portal to interconnect consumers, pharmacies, and wholesalers, where consumers are the primary imbibers for the pharmaceutical medications, pharmacies are the local distributors for the pharmaceutical medications, and wholesalers are the distributors for the pharmaceutical medications on a macro scale. The present invention is a cost effective and timely means for acquisition and distribution of pharmaceutical medications between consumers and pharmacies, between pharmacies and other pharmacies, and between pharmacies and wholesalers.

Figure 1:
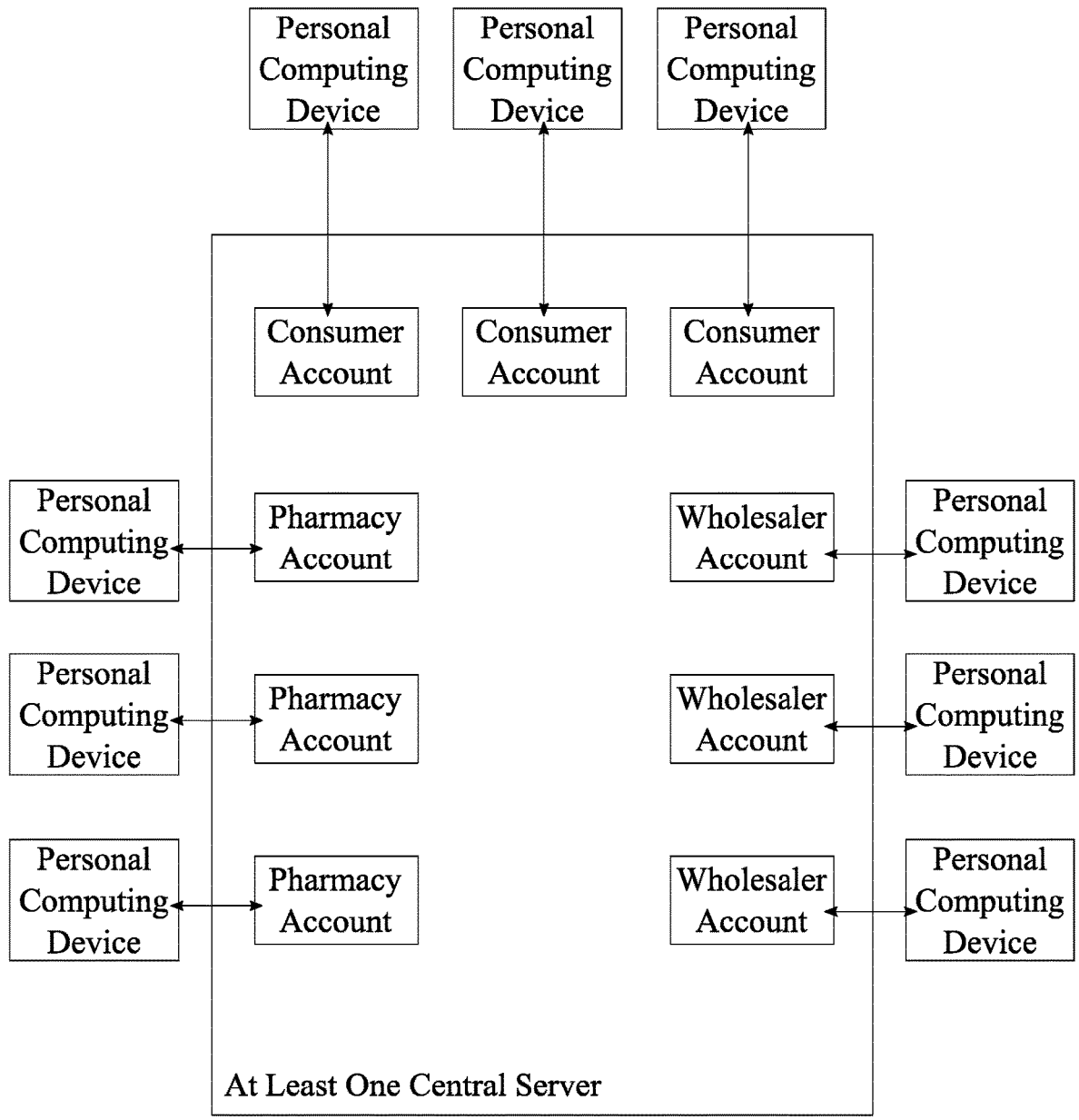
FIG. 1 is a schematic diagram detailing the communication connections between personal computing devices and an at least one central server.
Figure 2:
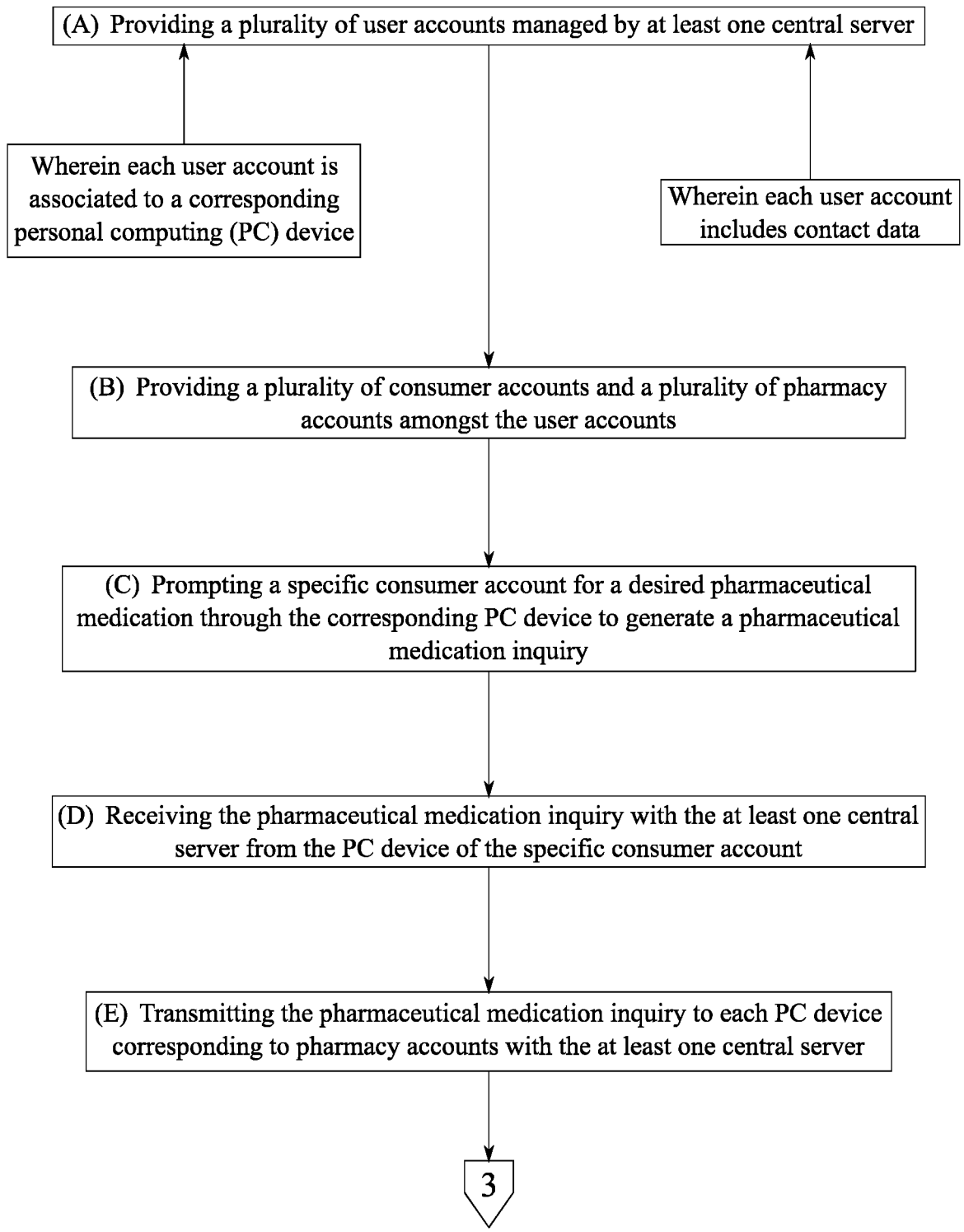
FIG. 2 is a flow diagram for the bidding processes between a specific consumer account and the plurality of pharmacy accounts.

In accordance to the preferred embodiment of the present invention, to implement the present invention, a plurality of user accounts is managed by at least one central server, wherein each user account is associated to a corresponding PC device and wherein each user account includes contact data (Step A), shown in FIG. 1 and FIG. 2. The at least one central server manages the online portal and executes functions for input and output of data to and from each PC device. PC devices include, but are not limited to, personal desktop computing devices, laptops, tablets, smart phones, or any appropriate device to with the ability execute a web browser. Contact data includes, but is not limited to, phone numbers, addresses, websites, or any other means of contacting the user of a particular user account of the plurality of user accounts. A plurality of consumer accounts and a plurality of pharmacy accounts are amongst the user accounts (Step B). Consumer accounts and pharmacy accounts are roles the user pick upon register to access discrete functionalities of the online portal.

Once a consumer registers through the online portal with the corresponding PC device to create a consumer account, the consumer is able to make an inquiry for a desired pharmaceutical medication and initiate a bidding process for the desired pharmaceutical medication. In the bidding process, the pharmacies offer the pharmaceutical medications at manageable prices, then the consumer decides to accept or reject the lowest bid. The bidding process is preferred to be blind such that neither participating party is able to discriminate against the other and a provides a market for reducing the price of pharmaceutical medications. Initially, a specific consumer account is prompted for a desired pharmaceutical medication through the corresponding PC device to generate a pharmaceutical inquiry (Step C) for the desired pharmaceutical medication, detailed in FIG. 2. The pharmaceutical medication inquiry is then received with the at least one central server from the PC device of the specific consumer account (Step D), such that the at least one central server is able to securely distribute the pharmaceutical medication inquiry to the PC device for each pharmacy account. The pharmaceutical medication inquiry includes the pharmaceutical medication name and the desired quantity of the pharmaceutical medication. Subsequently, the pharmaceutical medication inquiry is transmitted to the PC device corresponding to each pharmacy account with the at least one central server (Step E), in order for the pharmacy to assess the possibility for fulling the request and how much the pharmacy is willing to accept in payment.

Once the pharmacies have assessed the pharmaceutical medication inquiry, each pharmacy submits a pharmaceutical medication bid for the consumer to review in an attempt to sell the pharmaceutical medication at a competitive price. The pharmaceutical medication bid is received from the corresponding PC device from a subset of pharmacy accounts from the plurality of pharmacy accounts (Step F), shown in FIG. 3. If none of the plurality of pharmacy accounts respond with the pharmaceutical medication bid before a pre-determined time, preferably a week, the pharmaceutical medication bid is deleted, and the specific consumer account would need to resubmit the pharmaceutical medication inquiry. The subset of pharmacy accounts corresponds to pharmacies that are participating in the bidding process for the desired pharmaceutical medication. A lowest pharmaceutical medication bid amongst the subset of pharmacy accounts is then determined with the at least one central server (Step G), in order to provide the lowest offer to the consumer. Once the lowest pharmaceutical medication bid is determined, the lowest pharmaceutical bid is transmitted to the corresponding PC device of the specific consumer account with the at least one central sever (Step H) for the consumer to assess the lowest pharmaceutical bid.

Figure 3:
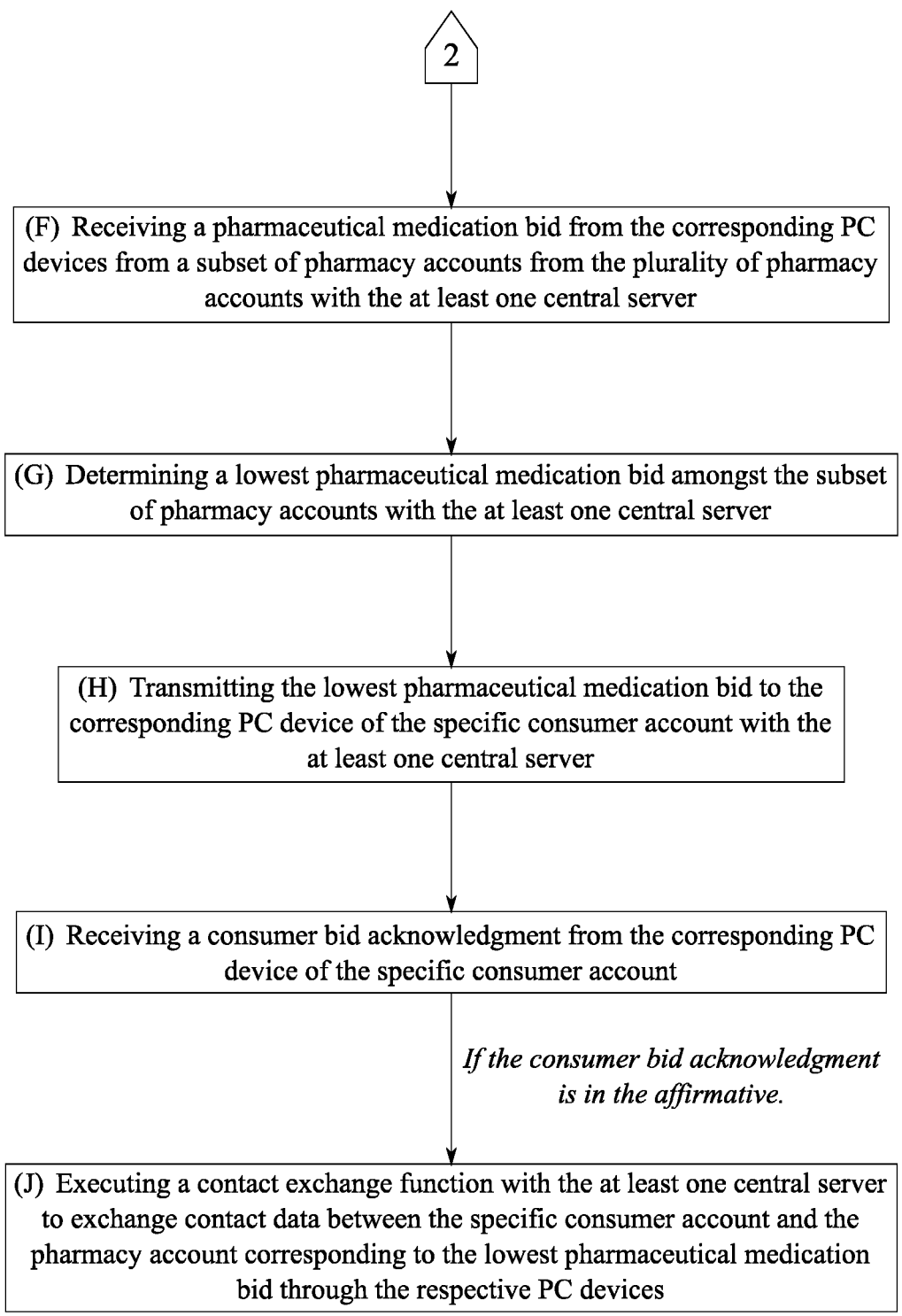
FIG. 3 is a continuation of the flow diagram for the diagram for the bidding processes between a specific consumer account and the plurality of pharmacy accounts from FIG. 2.

If the consumer accepts the bid, a consumer bid acknowledgement is received from the corresponding PC device of the specific consumer account with the at least one central server (Step I), detailed in FIG. 3. If the consumer bid acknowledgment is in the affirmative, a contact exchange function is executed with the at least one central server to exchange contact data between the specific consumer account and the pharmacy account corresponding to the lowest pharmaceutical medication bid through the respective PC devices (Step J). With the contact data exchanged, the user of the specific consumer account and the user of the pharmacy account corresponding to the lowest pharmaceutical medication bid are able to complete the transaction for the desired pharmaceutical medication. In accordance to the preferred embodiment, a monetary transaction function is executed between the PC device of the specific consumer account and the at least one central server before Step J for the service rendered by the present invention. In an alternate embodiment, a monetary transaction function is executed between the PC device of the pharmacy account corresponding to the lowest pharmaceutical medication bid and the at least one central server before Step J for the service rendered by the present invention.

The pharmacy is able to reserve the pharmaceutical medication associated with the specific consumer account on-site for a pre-determined time period for the specific consumer to obtain the pharmaceutical medication. If the specific consumer fails to obtain the pharmaceutical medication before the pre-determined time period elapses, the pharmacy may return the pharmaceutical medication to their inventory.

In some instances, the consumer requires a pharmaceutical medication within a critical period of time. Therefore, in accordance to the preferred embodiment of the present invention, an urgent medication tag is associated with the pharmaceutical medication inquiry, if the specific consumer requires the pharmaceutical medication expediently. If the urgent medication tag is associated with the pharmaceutical medication inquiry, the pharmaceutical medication inquiry is transmitted with priority to the PC device corresponding to each pharmacy account with the at least one central server, during Step E. The urgent medication tag is then prominently to the user of the PC device corresponding to each pharmacy account. Similar to other pharmaceutical medication inquiries, if none of the plurality of pharmacy accounts respond with the pharmaceutical medication bid before a pre-determined time, preferably within 4 hours, the pharmaceutical medication bid is deleted, such that the specific consumer is able to make other arrangements to obtain the necessary pharmaceutical medication.

Figure 4:
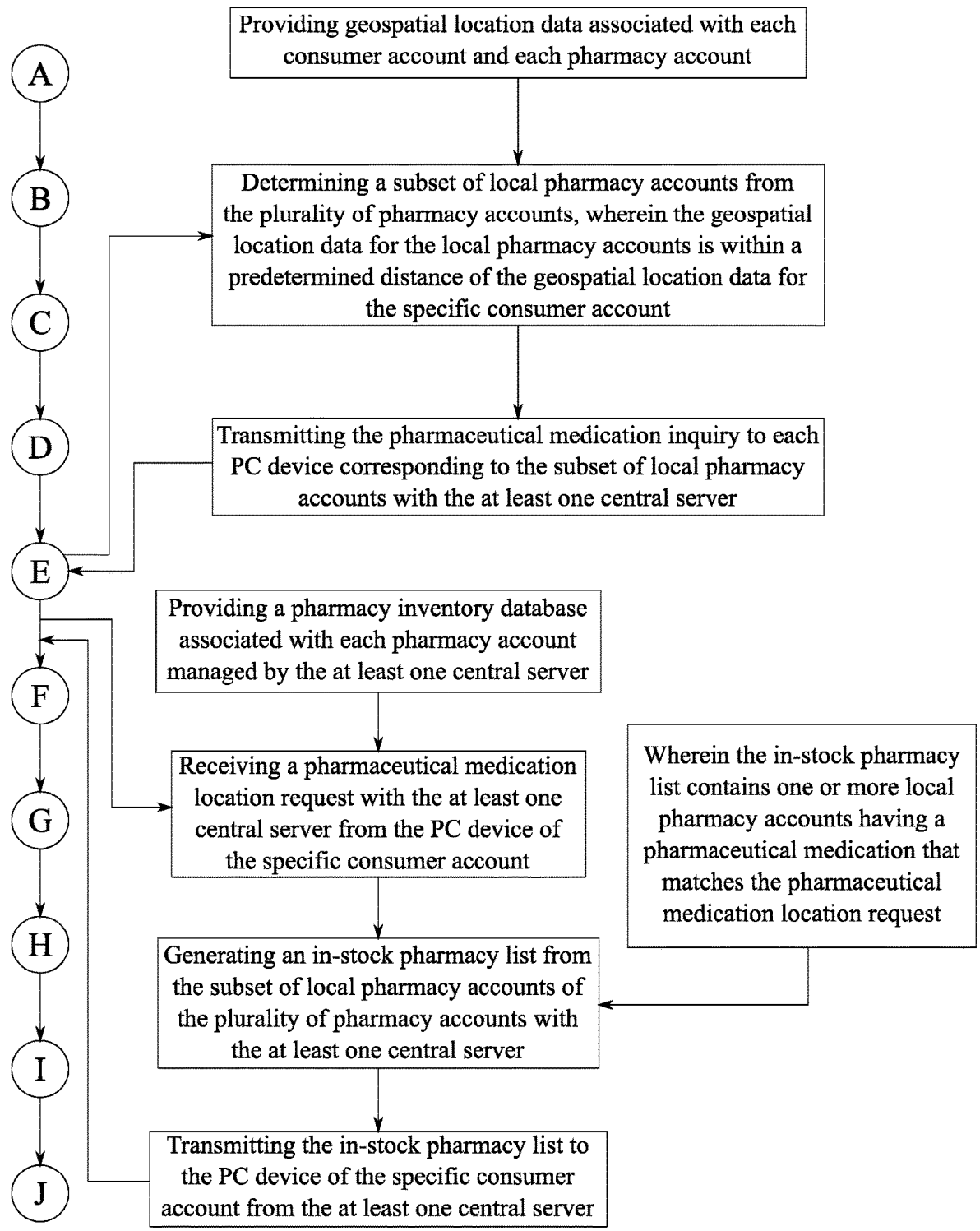
FIG. 4 is a flow diagram that details a process to locate pharmacies local to the user of the consumer account and a process to determine an in-stock pharmacy list for pharmacies where the pharmacy's inventory contains a desired pharmaceutical medication from a consumer account.

Further in accordance to the preferred embodiment of the present invention, geospatial data is associated with each consumer account and each pharmacy account to allow the at least one central server to determine the relative locations between a specific user and pharmacies local to the specific user. Illustrated in FIG. 4, a subset of local pharmacy accounts is determined from the plurality of pharmacy accounts, wherein the geospatial location data for the local pharmacy accounts is within a predetermined distance of the geospatial location data for the specific consumer account. Subsequently, the pharmaceutical medication inquiry is transmitted to each of PC device corresponding to the subset of local pharmacy accounts with the at least one central server, during Step E. Thus, the pharmaceutical medication inquiry is only transmitted to pharmacies within the predetermined distance of the consumer to allow the consumer to complete the transaction and obtain the pharmaceutical medication more conveniently.

In some embodiments of the present invention, the consumer is able to determine if the desired pharmaceutical medication is currently in stock at a local pharmacy. A pharmacy inventory database associated with each pharmacy account is managed by the at least one central server, in accordance to FIG. 4. A pharmaceutical medication location request is received with the at least one central server from the PC device of the specific consumer account as the consumer executes a search for the pharmaceutical medication. After the pharmaceutical medication location request is received, an in-stock pharmacy list is generated from the subset of local pharmacy accounts, wherein a pharmaceutical medication of the pharmaceutical medication location request matches a pharmaceutical medication of the pharmacy inventory database for each of the local pharmacy accounts. Thus, the in-stock pharmacy list is a list of pharmacies local to the consumer that have the desired pharmaceutical location in-stock and available for the consumer to obtain. The in-stock pharmacy list is transmitted to the PC device of the specific consumer account from the at least one server, such that the in-stock pharmacy list is able to be displayed to the consumer on the PC device of the specific consumer account. The consumer is then able to view local pharmacies where the desired pharmaceutical medication is able to be acquired.

Figure 5:
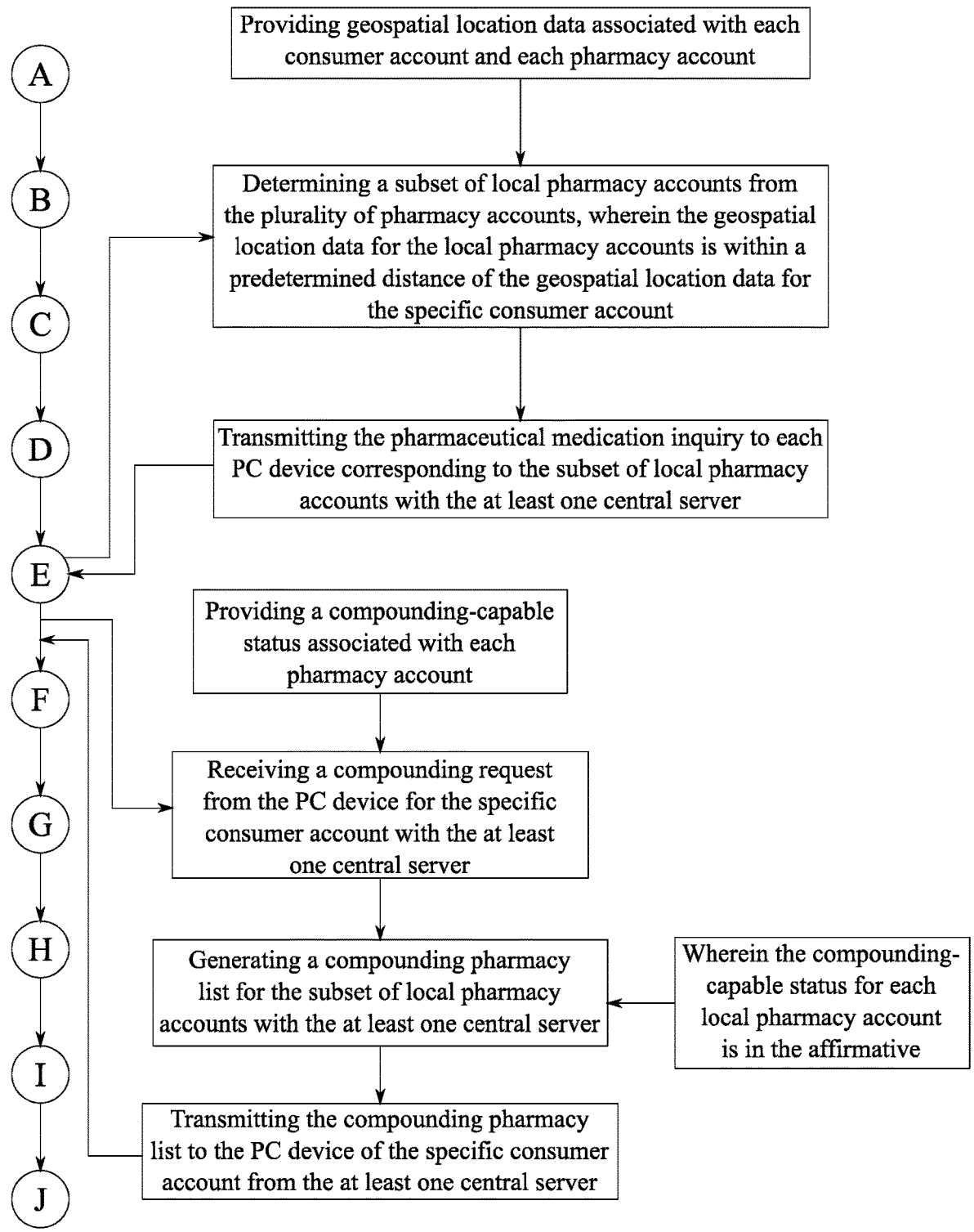
FIG. 5 is a flow diagram that details a process to locate pharmacies local to the user of the consumer account and a process to determine a compounding pharmacy list for pharmacies that are capable of compounding medications.

In some instances, a consumer may require a pharmacy that is capable of compounding, personalizing a pharmaceutical compound for a particular ailment from a plurality of pharmaceutical medications. To provide consumers with the ability to find a pharmacy capable of compounding, a compounding-capable status is associated with each pharmacy account, shown in FIG. 5. When the executes a function to determine compounding-capable pharmacies, a compounding request is received from the PC device for the specific consumer account with the central server. A compounding pharmacy list is then generated from the subset of local pharmacy accounts, wherein the compounding-capable status for each local pharmacy account is in the affirmative. Thus, the compounding pharmacy list is a list of pharmacies local to the consumer that are capable of compounding pharmaceutical compounds. The compounding pharmacy list is then transmitted to the PC device of the specific consumer account from the at least one central server, such that the consumer is able to view and assess the compounding pharmacy list to find a convenient local pharmacy to acquire necessary pharmaceutical compounds.

Figure 6:
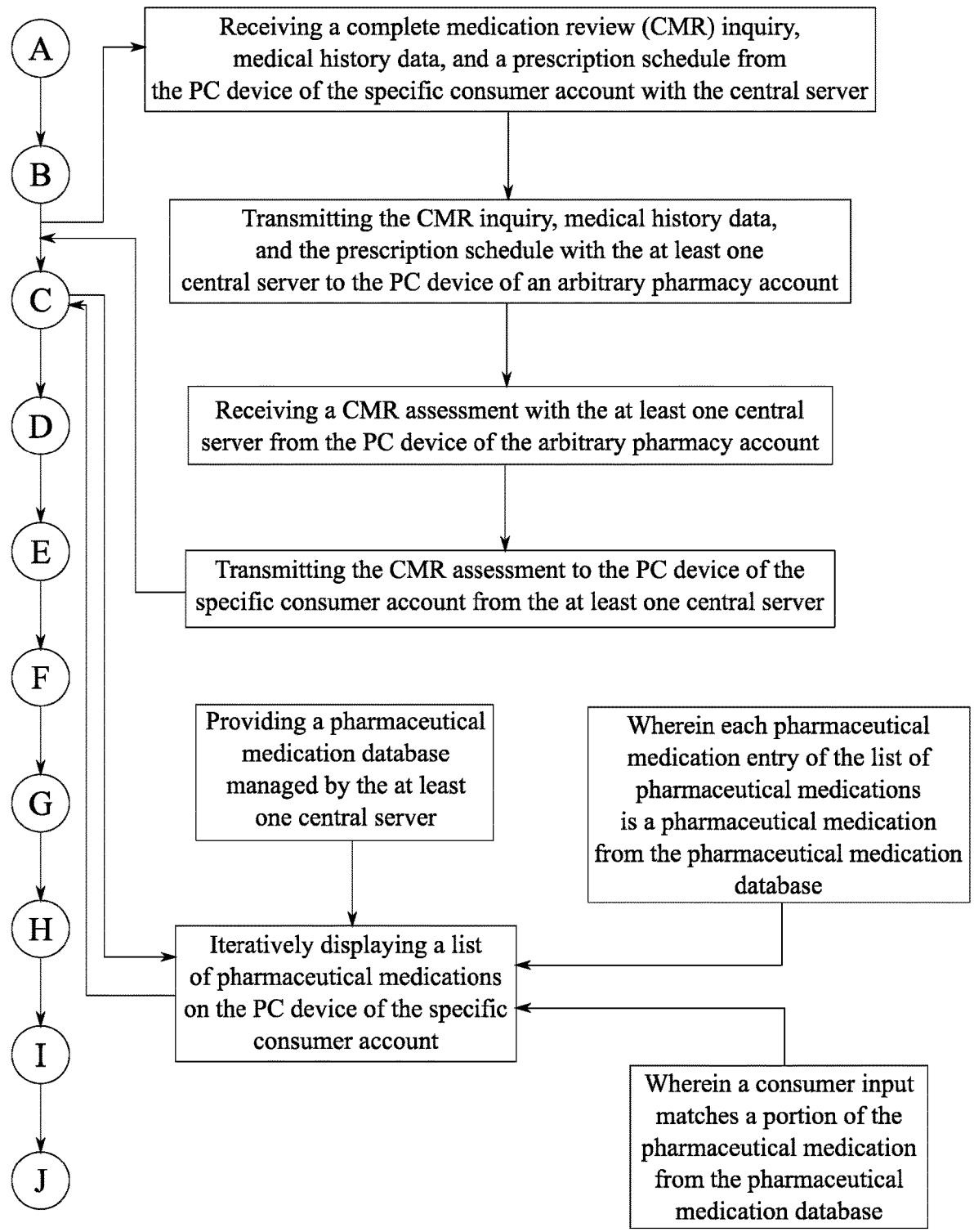
FIG. 6 is a flow diagram that details a process where a specific consumer account requests a complete medical review and details an iterative predictive search for pharmaceutical medications from a pharmaceutical medication database.

Further in accordance to the preferred embodiment, a pharmaceutical medication database is managed by the at least one server to be utilized in a predictive search algorithm, illustrated in FIG. 6. The predictive search algorithm assists the consumer in determining the proper pharmaceutical medication for the pharmaceutical medication inquiry. During a consumer's input, a list of pharmaceutical medications is iteratively displayed on the PC device of the specific consumer account, during Step C. Each pharmaceutical medication entry of the list of pharmaceutical medications is a pharmaceutical medication from the pharmaceutical medication database, wherein the consumer input matches a portion of the pharmaceutical medication from the pharmaceutical medication database. Thus, as the consumer inputs the name of a pharmaceutical medication, a list of pharmaceutical medications is generated predicting the complete pharmaceutical medication name. The predictive search algorithm reduces input error and allows the consumer to find the correct pharmaceutical medication more efficiently to be used in the pharmaceutical medication inquiry.

As many pharmaceutical medications may have adverse interactions when imbibed, a consumer may desire to request a complete medication review (CRM) to assess the interactions between pharmaceutical medications currently being taken, prescribed pharmaceutical medications, and the consumer's medical history. In some embodiments of the present invention, a CMR inquiry, medical history data, and a prescription schedule is received from the PC device of the specific consumer account with the central server, illustrated in FIG. 6. The CMR inquiry, medical history data, and the prescription schedule is transmitted with the at least one central server to the PC device of an arbitrary pharmacy account. Any pharmacist should be able to assist the consumer with reviewing the consumer's medical history data and the prescription schedule to determine any possible conflicts between pharmaceutical medications or provide recommendations for alternative pharmaceutical medications. A CMR assessment is then received with the at least one central server from the PC device of the arbitrary pharmacy account, wherein the CMR assessment contains the recommendation or potential conflicts from the pharmacist. The CMR assessment is then transmitted to the PC device of the specific consumer account from the at least one server, such that the consumer is able to review the CMR assessment and take actions accordingly.

Figure 7:
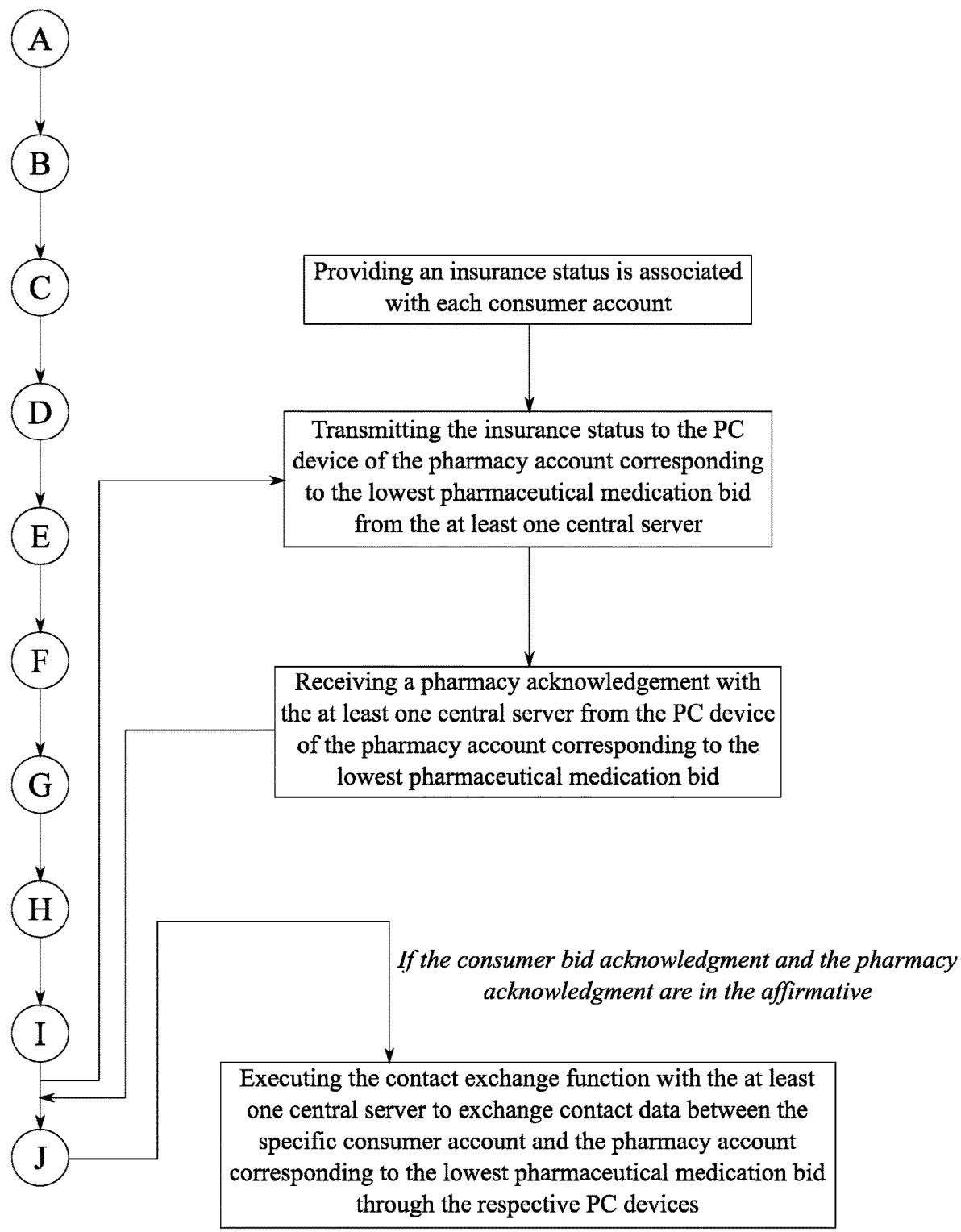
FIG. 7 is a flow diagram that details a process for a pharmacy to acknowledge an insurance status associated with the specific consumer account.

For a plurality of pharmacies, whether or not a consumer has insurance makes the difference between the pharmacy profiting from a pharmaceutical medication transaction or not. In some embodiments of the present invention, an insurance status is associated with each consumer account, shown in FIG. 7. Before Step J, the insurance status is transferred to the PC device of the pharmacy account corresponding to the lowest pharmaceutical medication bid with the at least one central server. The pharmacy determines whether or not a transaction for the desired pharmaceutical medication is acceptable or not and responds with a pharmacy acknowledgment. The pharmacy acknowledgement is received with the at least one central server from the PC device of the pharmacy account corresponding to the lowest pharmaceutical bid. If the consumer bid acknowledgment and the pharmacy acknowledgment are in the affirmative, the contact exchange function is then executed with the at least one central server to exchange contact data between the specific consumer account and the pharmacy account corresponding to the lowest pharmaceutical medication bid through the respective PC devices, during Step J. Thus, the consumer and the pharmacy mutually benefit from the pharmaceutical medication transaction.

Figure 8:
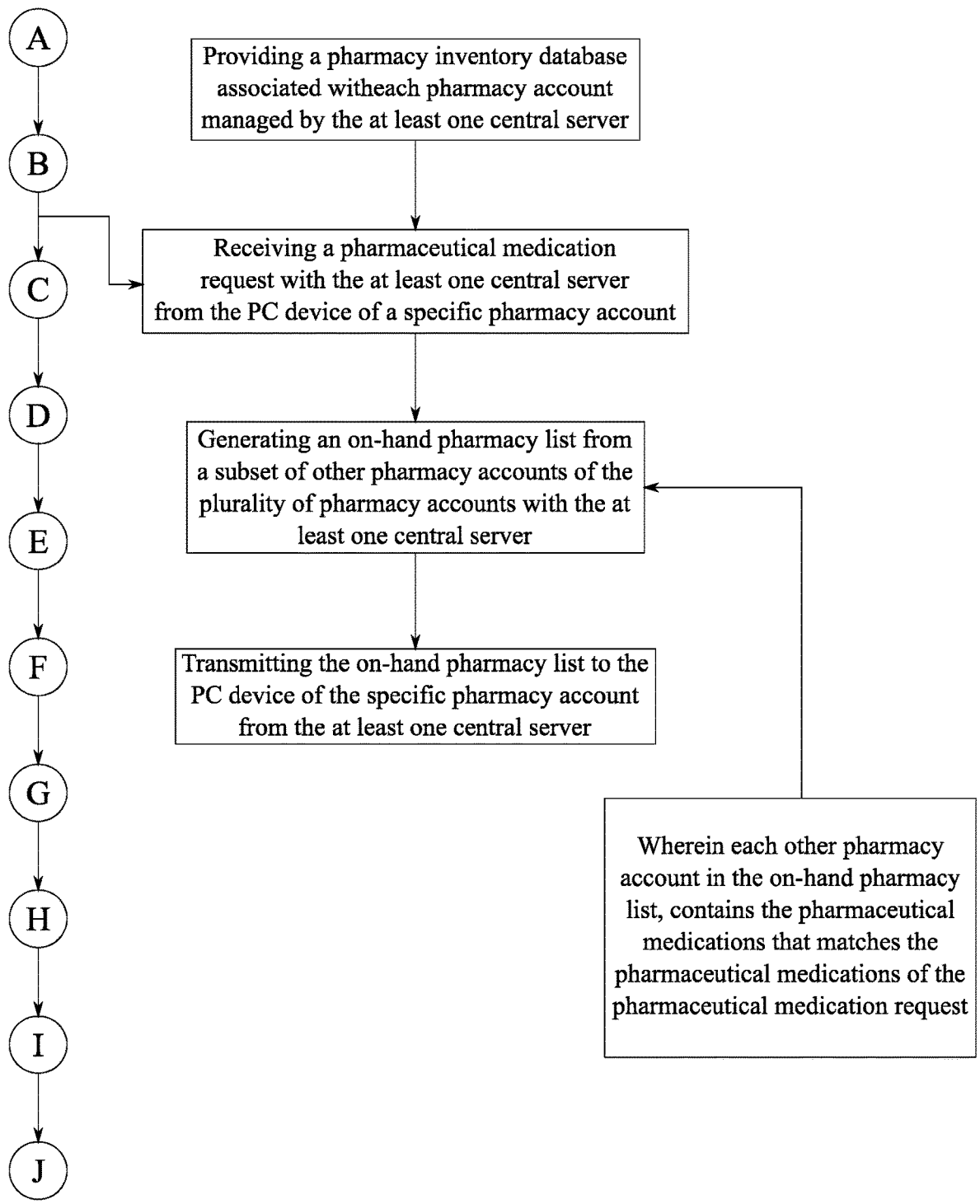
FIG. 8 is a flow diagram that details a process to determine an on-hand pharmacy list for pharmacies where the pharmacy's inventory contains a desired pharmaceutical medication from a pharmacy account.

Similar to the specific consumer account, a user for a specific pharmacy account is able to determine if other pharmacies have a desired pharmaceutical medication in stock. A pharmaceutical medication request is received with the at least one central server from the PC device of the specific pharmacy account for the desired pharmaceutical medication, in accordance to FIG. 8. An on-hand pharmacy list is then generated from a subset of other pharmacy accounts of the plurality of pharmacy accounts with the at least one central server. For each other pharmacy account of the subset of pharmacy accounts, the pharmaceutical medications of the pharmaceutical medication request match pharmaceutical medications of the corresponding pharmacy inventory database, such that the desired pharmaceutical medications are known to be in the inventory for each of the subset of other pharmacy accounts. The on-hand pharmacy list is then transmitted to the PC device of the specific pharmacy account from the at least one central server, such that the user of the specific pharmacy account is able to review the on-hand pharmacy list to locate and arrange the desired pharmaceutical medication to be acquired.

Figure 9:
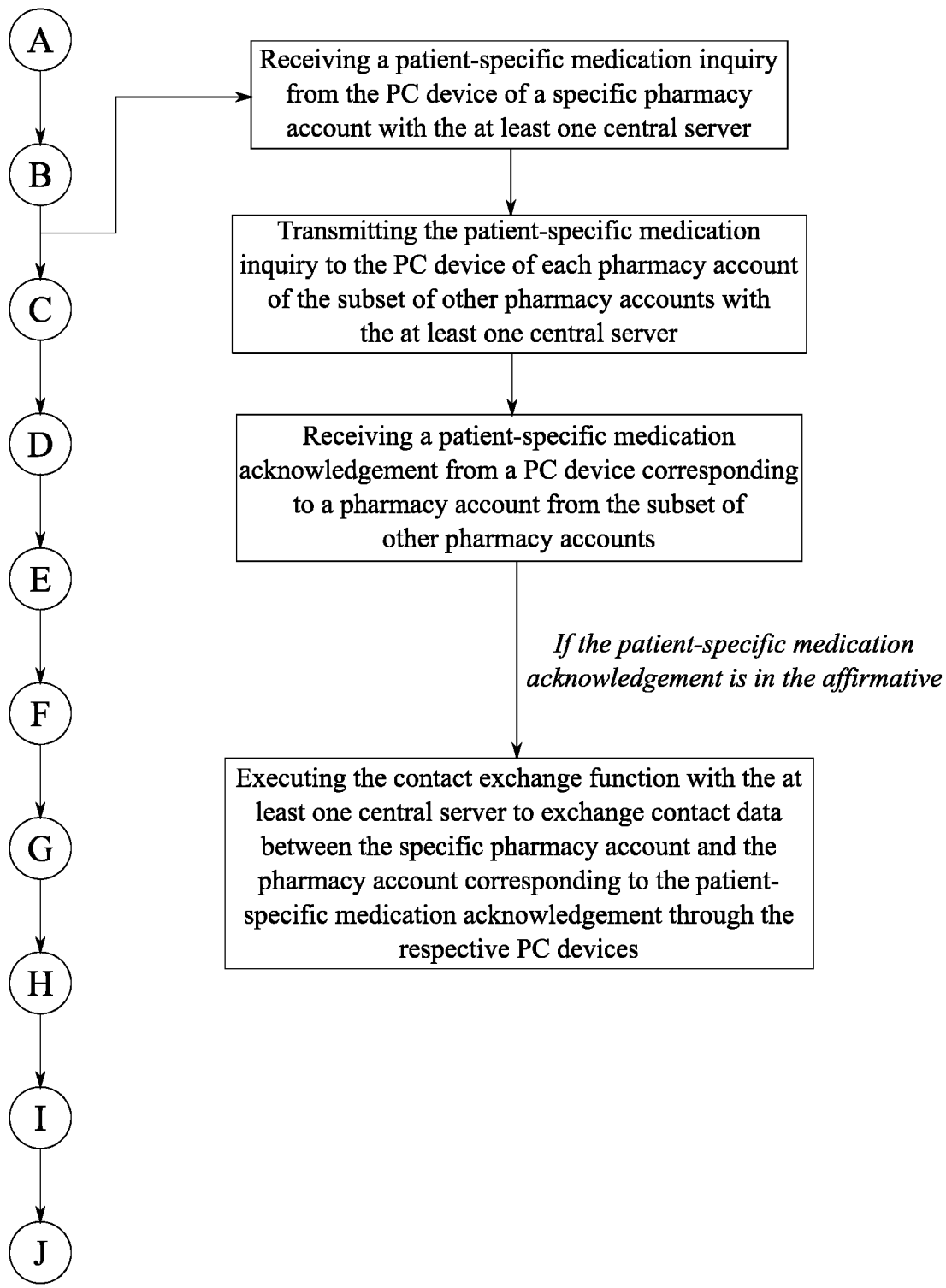
FIG. 9 is a flow diagram that details a process for obtaining patient-specific medication between pharmacy accounts.

More specifically, the pharmacy is able to obtain pharmaceutical medications from other pharmacies to fulfill a specific patient need. A patient-specific medication inquiry is received from the PC device of the specific pharmacy account with the at least one central server, detailed in FIG. 9. The patient-specific medication inquiry is then transmitted to the PC device for each pharmacy account of the subset of other pharmacy accounts with the at least one central server for the users corresponding to each of the subset of other pharmacy accounts is able to assess the inquiry. A patient-specific medication acknowledgement is then received from a PC device corresponding to a pharmacy account from the subset of the other pharmacy accounts. If the patient-specific medication acknowledgement is in the affirmative, the contact exchange function is executed with the at least one central server to exchange contact data between the specific pharmacy account and the pharmacy account corresponding to the patient specific medication acknowledgement through the respective PC devices. Therefore, the user of the specific pharmacy account is able to confirm that the user of the pharmacy account corresponding to the patient specific medication acknowledgement would have the patient-specific medication accessible for the user of the specific pharmacy account to obtain.

Figure 10:
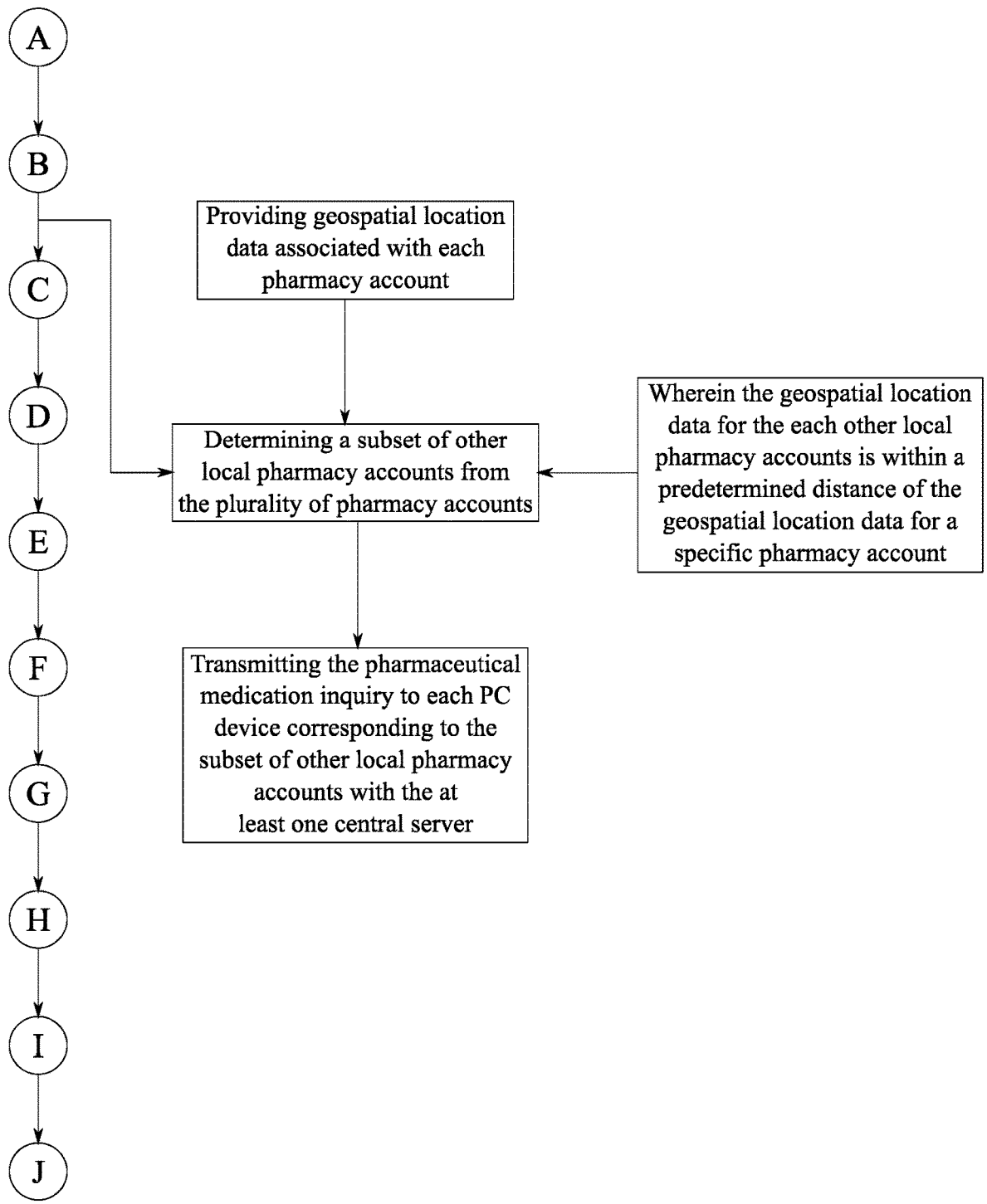
FIG. 10 is a flow diagram that details a process for pharmacies to locate other local pharmacy accounts.

Additionally, the user of the pharmacy account is able to assess whether or not another pharmacy is within an accessible distance from the physical location of that user's pharmacy. In accordance to FIG. 10, a subset of other local pharmacy accounts from the plurality of pharmacy accounts is determined, wherein the geospatial location data for each other local pharmacy account is within a predetermined distance of the geospatial data for the specific pharmacy account. The pharmaceutical medication inquiry is then transmitted to each PC device corresponding to the subset of other local pharmacy accounts with the at least one server. Therefore, the pharmaceutical medication inquiry is restricted to logistically accessible pharmacies for the user of the specific pharmacy account to obtain the pharmaceutical medication. Similarly, the patient-specific medication inquiry is able to be restricted to being transmitted to each PC device corresponding to the subset of other local pharmacy accounts with the at least one server, such that the patient-specific medication is logistically accessible.

Figure 11:
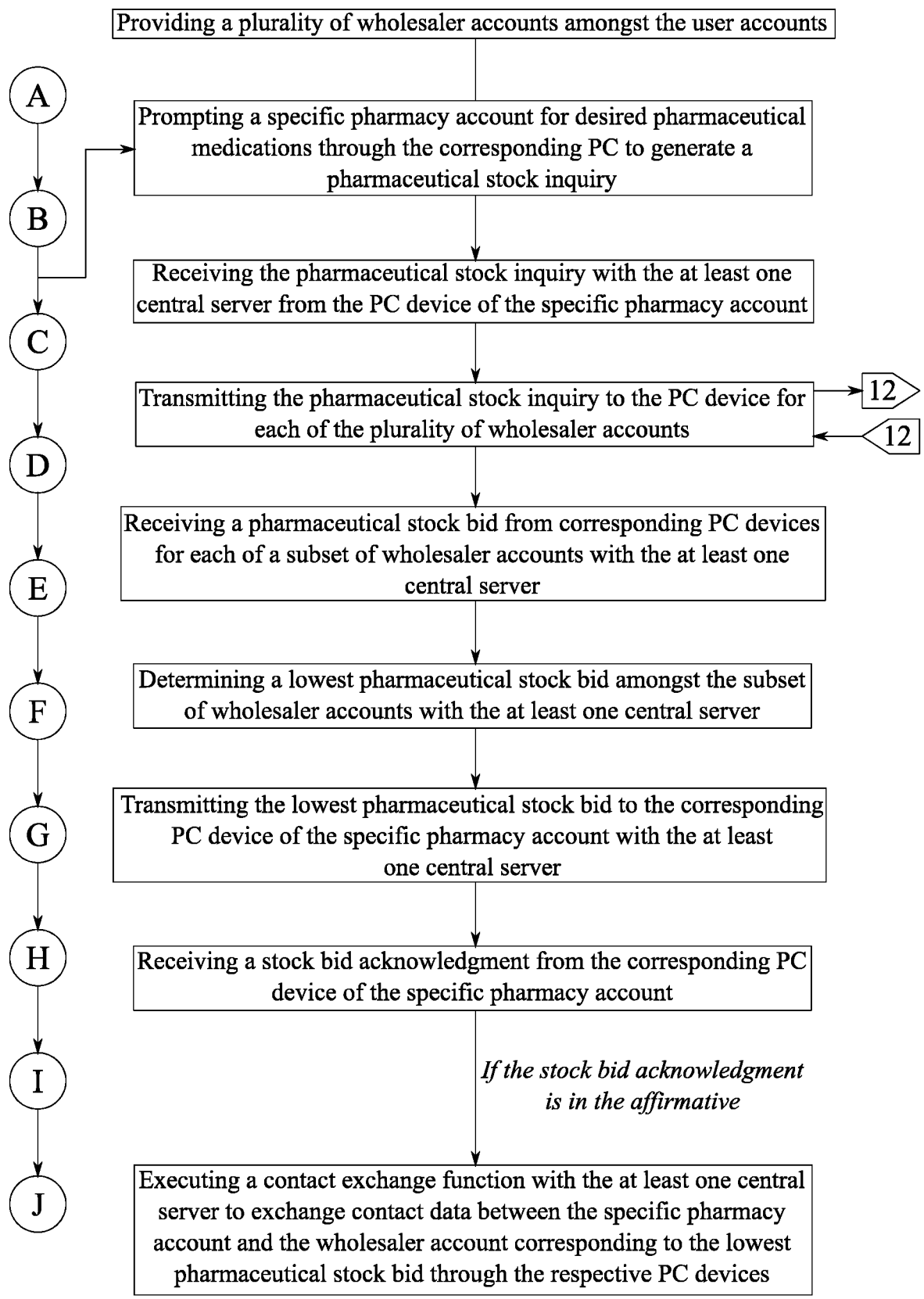
FIG. 11 is a flow diagram that details a process for pharmacies to engage in a bid for pharmaceutical medication with a plurality of wholesaler accounts.

Further in accordance to the preferred embodiment of the present invention, a plurality of wholesaler accounts is amongst the user accounts, detailed in FIG. 11. The wholesalers associated with each wholesaler account provide pharmacies with shipments for a plurality of pharmaceutical medications to replenish pharmacy inventories over a large geographical region. Similar to the bidding process between the specific consumer account and the plurality of pharmacy accounts, a specific pharmacy account is able to initiate a bidding process with the plurality of wholesaler accounts. The specific pharmacy is prompted for desired chemical compounds through the corresponding PC to generate a pharmaceutical stock inquiry. The pharmaceutical stock inquiry is a shipping order for the desired pharmaceutical medications to restock the inventory of the pharmacy associated with the specific pharmacy account. The pharmaceutical stock inquiry is then received with the at least one central server from the PC device of the specific pharmacy account. Subsequently, the pharmaceutical stock inquiry is then transmitted to PC device for each of the plurality of wholesaler accounts. The wholesalers assess the feasibility of fulfilling the pharmaceutical stock inquiry to submit a pharmaceutical stock bid to engage in the transaction. The pharmaceutical stock bid is received from the corresponding PC devices for each of a subset of wholesaler accounts with the at least one server, wherein the subset of wholesaler accounts are wholesalers that desire to engage in the transaction of the desired pharmaceutical medications. A lowest pharmaceutical stock bid is then determined amongst the subset of wholesaler accounts with the at least one central server to provide the specific pharmacy with the lowest price point for the desired pharmaceutical medications. The lowest pharmaceutical stock bid is then transmitted to the corresponding PC device of the specific pharmacy account with the at least one central server to allow the user of the specific pharmacy account to assess the lowest pharmaceutical stock bid and respond with a stock bid acknowledgement to accept or reject the transaction. The stock bid acknowledgement is then received from the corresponding PC device of the specific pharmacy account. If the stock bid acknowledgment is in the affirmative, a contact exchange function is executed with the at least one central server to exchange contact data between the specific pharmacy account and the wholesaler account corresponding to the lowest pharmaceutical stock bid through the respective PC devices. With the contact data exchanged, the user of the specific pharmacy account and the user of the wholesaler account corresponding to the lowest pharmaceutical stock bid are able to complete the transaction for the desired pharmaceutical medication. In accordance to the preferred embodiment, the monetary transaction function is executed between the PC device of the specific pharmacy account and the at least one central server. In an alternate embodiment of the present invention, the monetary transaction function is executed between the PC device of the pharmacy account corresponding to the lowest pharmaceutical replenishment bid and the at least one central server for the service rendered by the present invention.

Figure 12:
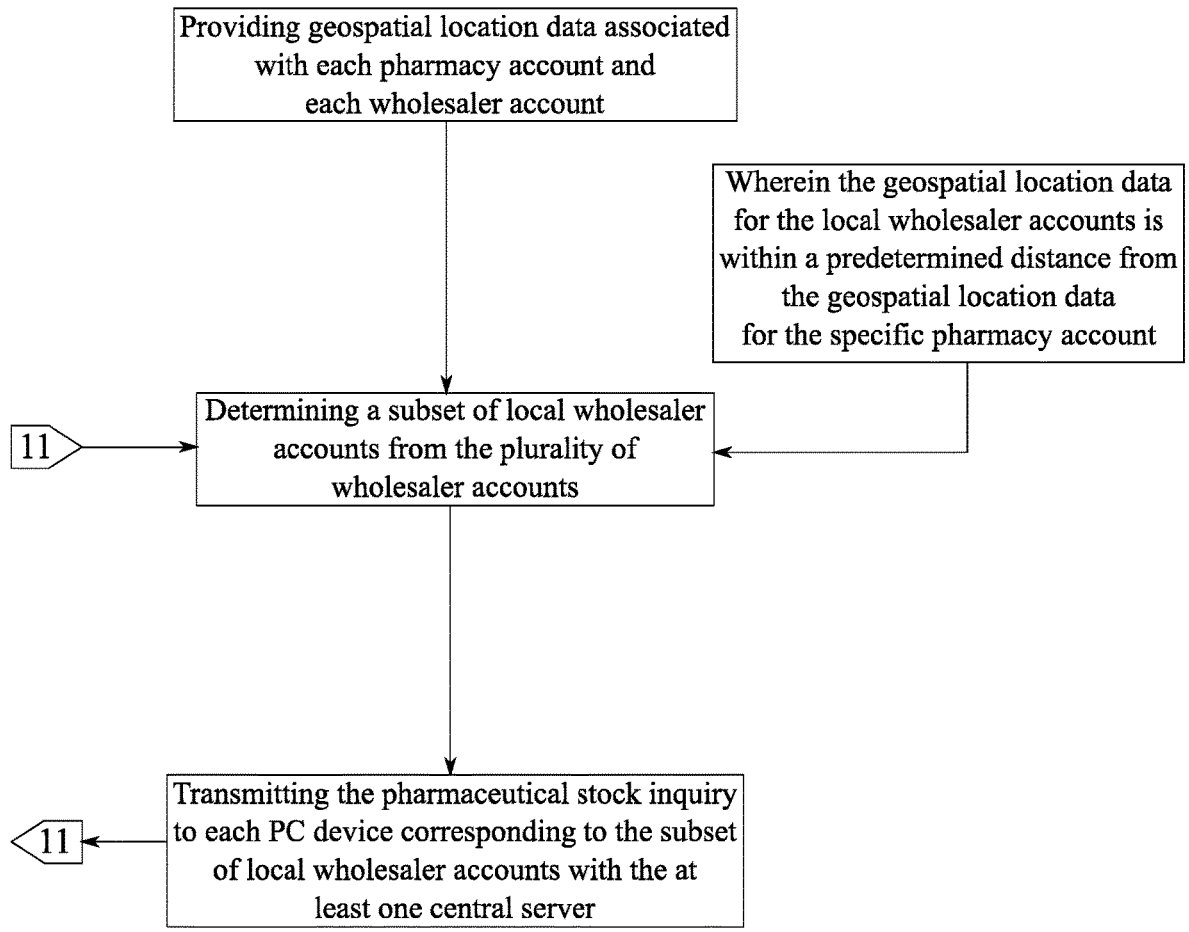
FIG. 12 is a flow diagram that details a process for pharmacies to determine local wholesalers from the plurality of wholesalers during the process outlined in FIG. 11.

In accordance to the preferred embodiment of the present invention, pharmacies can provide a predetermined distance that the wholesaler must be located within to efficiently acquire pharmaceutical medications, shown in FIG. 12. Geospatial location data is additionally associated with each wholesaler account. A subset of local wholesaler accounts is determined from the plurality of wholesaler accounts, wherein the geospatial location data for the local wholesaler accounts is within the predetermined distance from the geospatial location data for the specific pharmacy account. The pharmaceutical stock inquiry is then transmitted to each PC device corresponding to the subset of local wholesaler accounts with the at least one server. Thus, wholesalers which are able to participate in the bidding process are limited to a range within the predetermined distance from the user of specific pharmacy account.

Figure 13:
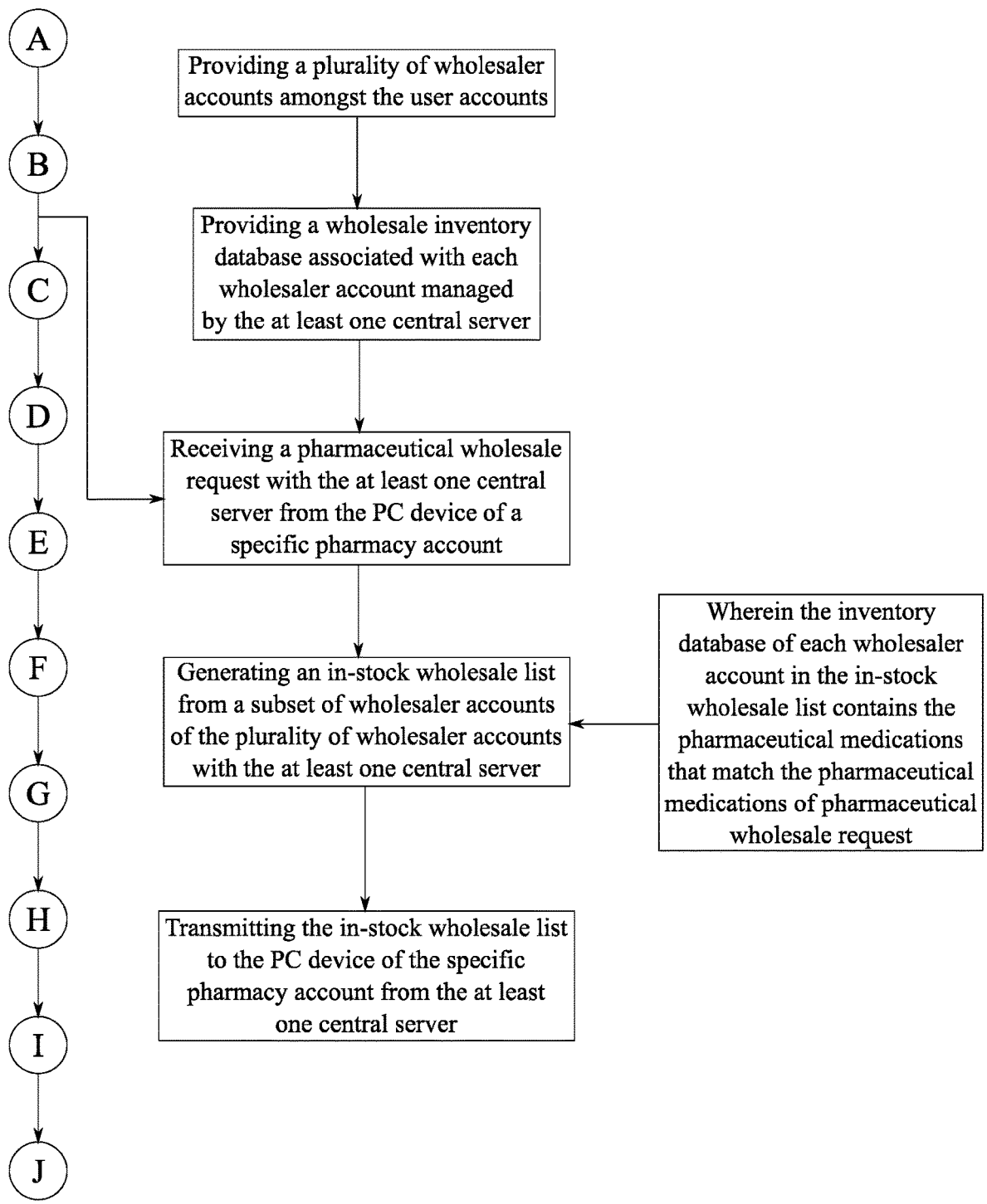
FIG. 13 is a flow diagram that details a process to determine an in-stock wholesaler list for wholesalers where the wholesaler's inventory contains a desired pharmaceutical medication from a pharmacy account.

Similar to a consumer's ability to determine if the desired pharmaceutical medication is currently in stock at a local pharmacy, a pharmacy is able to determine if desired pharmaceutical is able to be obtained from a local wholesaler. A wholesaler inventory database is associated with each wholesaler account managed by the at least one central server, shown in FIG. 13. Each wholesaler inventory database includes pharmaceutical medications which are deliverable from the corresponding wholesaler. A pharmaceutical wholesale request is received with the at least one central server from the PC device of the specific account. An in-stock wholesale list is generated from a subset of wholesaler accounts of the plurality of wholesaler accounts with the at least one central server, wherein pharmaceutical medications of the pharmaceutical wholesale request are found within pharmaceutical medications of the wholesale inventory database for each wholesaler account of the subset of wholesaler accounts. The in-stock wholesale list is then transmitted to the PC device of the specific pharmacy account from the at least one central server, such that the user of the specific pharmacy account is able to locate wholesalers which have the desired pharmaceutical medications in stock.

Although the invention has been explained in relation to its preferred embodiment, it is to be understood that many other possible modifications and variations can be made without departing from the spirit and scope of the invention as hereinafter claimed.

What is claimed is:

1. A method for managing a pharmaceutical supply chain comprising:

(A) providing a plurality of user accounts managed by at least one central server, wherein each user account is associated to a corresponding personal computing (PC) device and wherein each user account includes contact data;

(B) providing a plurality of consumer accounts and a plurality of pharmacy accounts amongst the user accounts;

providing a plurality of wholesaler accounts amongst the user accounts;

prompting a specific pharmacy account for desired pharmaceutical medications through the corresponding PC to generate a pharmaceutical stock inquiry;

receiving the pharmaceutical stock inquiry with the at least one central server from the PC device of the specific pharmacy account;

transmitting the pharmaceutical stock inquiry to the PC device for each of the plurality of wholesaler accounts;

receiving a pharmaceutical stock bid from corresponding PC devices for each of a subset of wholesaler accounts with the at least one central server;

determining a lowest pharmaceutical stock bid amongst the subset of wholesaler accounts with the at least one central server;

transmitting the lowest pharmaceutical stock bid to the corresponding PC device of the specific pharmacy account with the at least one central server;

receiving a stock bid acknowledgment from the corresponding PC device of the specific pharmacy account;

executing a contact exchange function with the at least one central server to exchange contact data between the specific pharmacy account and the wholesaler account corresponding to the lowest pharmaceutical stock bid through the respective PC devices, if the stock bid acknowledgment is in the affirmative;

(C) prompting a specific consumer account for a desired pharmaceutical medication through the corresponding PC device to generate a pharmaceutical medication inquiry;

receiving a complete medication review (CMR) inquiry, medical history data, and a prescription schedule from the PC device of the specific consumer account with the central server;

transmitting the CMR inquiry, medical history data, and the prescription schedule with the at least one central server to the PC device of an arbitrary pharmacy account;

receiving a CMR assessment with the at least one central server from the PC device of the arbitrary pharmacy account;

transmitting the CMR assessment to the PC device of the specific consumer account from the at least one central server;

(D) receiving the pharmaceutical medication inquiry with the at least one central server from the PC device of the specific consumer account;

(E) transmitting the pharmaceutical medication inquiry to each PC device corresponding to pharmacy accounts with the at least one central server;

(F) receiving a pharmaceutical medication bid from the corresponding PC devices from a subset of pharmacy accounts from the plurality of pharmacy accounts with the at least one central server;

(G) determining a lowest pharmaceutical medication bid amongst the subset of pharmacy accounts with the at least one central server;

(H) transmitting the lowest pharmaceutical medication bid to the corresponding PC device of the specific consumer account with the at least one central server;

(I) receiving a consumer bid acknowledgment from the corresponding PC device of the specific consumer account;

providing an insurance status is associated with each consumer account;

transmitting the insurance status to the PC device of the pharmacy account corresponding to the lowest pharmaceutical medication bid from the at least one central server;

receiving a pharmacy acknowledgement with the at least one central server from the PC device of the pharmacy account corresponding to the lowest pharmaceutical medication bid; and (J) executing a contact exchange function with the at least one central server to exchange contact data between the specific consumer account and the pharmacy account corresponding to the lowest pharmaceutical medication bid through the respective PC devices, if the consumer bid acknowledgment and the pharmacy acknowledgment are in the affirmative.

2. The method of for managing a pharmaceutical supply chain, as claimed in claim 1, comprising:

providing geospatial location data associated with each consumer account and each pharmacy account;

determining a subset of local pharmacy accounts from the plurality of pharmacy accounts, wherein the geospatial location data for the local pharmacy accounts is within a predetermined distance of the geospatial location data for the specific consumer account; and transmitting the pharmaceutical medication inquiry to each PC device corresponding to the subset of local pharmacy accounts with the at least one central server, during Step E.

3. The method of for managing a pharmaceutical supply chain, as claimed in claim 2, comprising:

providing a pharmacy inventory database associated with each pharmacy account managed by the at least one central server;

receiving a pharmaceutical medication location request with the at least one central server from the PC device of the specific consumer account;

generating an in-stock pharmacy list from the subset of local pharmacy accounts of the plurality of pharmacy accounts with the at least one central server, wherein a pharmaceutical medication of the pharmaceutical medication location request matches a pharmaceutical medication of the pharmacy database for each of the local pharmacy accounts; and transmitting the in-stock pharmacy list to the PC device of the specific consumer account from the at least one central server.

4. The method of for managing a pharmaceutical supply chain, as claimed in claim 2, comprising:

providing a compounding-capable status associated with each pharmacy account;

receiving a compounding request from the PC device for the specific consumer account with the at least one central server;

generating a compounding pharmacy list for the subset of local pharmacy accounts with the at least one central server, wherein the compounding-capable status for each local pharmacy account is in the affirmative; and transmitting the compounding pharmacy list to the PC device of the specific consumer account from the at least one central server.

5. The method of for managing a pharmaceutical supply chain, as claimed in claim 1, comprising:

providing a pharmaceutical medication database managed by the at least one central server; and iteratively displaying a list of pharmaceutical medications on the PC device of the specific consumer account, during Step C, wherein each pharmaceutical medication entry of the list of pharmaceutical medications is a pharmaceutical medication from the pharmaceutical medication database and wherein a consumer input matches a portion of the pharmaceutical medication from the pharmaceutical medication database.

6. The method of for managing a pharmaceutical supply chain, as claimed in claim 1, comprising:

providing a pharmacy inventory database associated with each pharmacy account managed by the at least one central server;

receiving a pharmaceutical medication request with the at least one central server from the PC device of a specific pharmacy account;

generating an on-hand pharmacy list from a subset of other pharmacy accounts of the plurality of pharmacy accounts with the at least one central server, wherein pharmaceutical medications of the pharmaceutical medication request match pharmaceutical medications of the pharmacy inventory database for each other pharmacy account of the subset of other pharmacy accounts; and transmitting the on-hand pharmacy list to the PC device of the specific pharmacy account from the at least one central server.

7. The method of for managing a pharmaceutical supply chain, as claimed in claim 1, comprising:

receiving a patient-specific medication inquiry from the PC device of a specific pharmacy account with the at least one central server;

transmitting the patient-specific medication inquiry to the PC device of each pharmacy account of the subset of other pharmacy accounts with the at least one central server;

receiving a patient-specific medication acknowledgement from a PC device corresponding to a pharmacy account from the subset of other pharmacy accounts;

executing the contact exchange function with the at least one central server to exchange contact data between the specific pharmacy account and the pharmacy account corresponding to the patient-specific medication acknowledgement through the respective PC devices, if the patient-specific medication acknowledgement is in the affirmative.

8. The method of for managing a pharmaceutical supply chain, as claimed in claim 1, comprising:

providing geospatial location data associated with each pharmacy account;

determining a subset of other local pharmacy accounts from the plurality of pharmacy accounts, wherein the geospatial location data for the each other local pharmacy accounts is within a predetermined distance of the geospatial location data for a specific pharmacy account; and transmitting the pharmaceutical medication inquiry to each PC device corresponding to the subset of other local pharmacy accounts with the at least one central server.

9. The method of for managing a pharmaceutical supply chain, as claimed in claim 7, comprising:

providing geospatial location data associated with each pharmacy account and each wholesaler account;

determining a subset of local wholesaler accounts from the plurality of wholesaler accounts, wherein the geospatial location data for the local wholesaler accounts is within a predetermined distance from the geospatial location data for the specific pharmacy account; and transmitting the pharmaceutical stock inquiry to each PC device corresponding to the subset of local wholesaler accounts with the at least one central server.

10. The method for managing a pharmaceutical supply chain, as claimed in claim 1, comprising:

providing a plurality of wholesaler accounts amongst the user accounts;

providing a wholesale inventory database associated with each wholesaler account managed by the at least one central server;

receiving a pharmaceutical wholesale request with the at least one central server from the PC device of a specific pharmacy account;

generating an in-stock wholesale list from a subset of wholesaler accounts of the plurality of wholesaler accounts with the at least one central server, wherein pharmaceuticals compounds of the pharmaceutical wholesale request match pharmaceutical medications of the wholesale inventory database for each wholesaler account of the subset of wholesaler accounts; and transmitting the in-stock wholesale list to the PC device of the specific pharmacy account from the at least one central server.

* * * * *